United States Patent
Wang et al.

(10) Patent No.: US 8,673,343 B2
(45) Date of Patent: Mar. 18, 2014

(54) PREPARATION AND ADMINISTRATION OF JOJOBA PRODUCT FOR REDUCING WEIGHT, FAT AND BLOOD LIPID LEVELS AND FOR THE PREVENTION AND TREATMENT OF CANCER

(75) Inventors: Yibing Wang, Gilbert, AZ (US); Peter J. Reilly, Scottsdale, AZ (US); Yihong Wang, Jinan (CN)

(73) Assignee: Yiwu Jiangr Bio-Technology HK Corp., Hong Kong (HK)

( * ) Notice: Subject to any disclaimer, the term of this patent is extended or adjusted under 35 U.S.C. 154(b) by 1627 days.

(21) Appl. No.: 11/536,920

(22) Filed: Sep. 29, 2006

(65) Prior Publication Data

US 2007/0026091 A1 Feb. 1, 2007

Related U.S. Application Data

(60) Division of application No. 10/212,577, filed on Aug. 5, 2002, now Pat. No. 7,138,134, which is a continuation-in-part of application No. 10/066,164, filed on Feb. 1, 2002, now abandoned.

(30) Foreign Application Priority Data

Dec. 18, 2001 (CN) .................. 01 1 35290

(51) Int. Cl.
*A61K 47/00* (2006.01)
*A61F 13/00* (2006.01)
*C08B 37/00* (2006.01)

(52) U.S. Cl.
USPC .............................. 424/439; 127/36; 424/434

(58) Field of Classification Search
None
See application file for complete search history.

(56) References Cited

U.S. PATENT DOCUMENTS 5,626,849 A 5/1997 Hastings et al.
5,962,043 A 10/1999 Jones et al.
(Continued)

FOREIGN PATENT DOCUMENTS

| WO | 9425035 | 11/1994 | |
| WO | WO 99/62451 | * 12/1999 | ............. A61F 31/02 |
| WO | 0072861 | 12/2000 | |

OTHER PUBLICATIONS

Benzioni, Aliza; "New Crop FactSHEET" for Jojoba; Purdue University Center for New Crops & Plant Products; http://www.hort.purdue.edu/newcrop/cropfactsheets/jojoba.html; (1997).*

(Continued)

*Primary Examiner* — Robert A Wax
*Assistant Examiner* — Jeffrey T Palenik
(74) *Attorney, Agent, or Firm* — Robert D. Atkins; Patent Law Group: Atkins & Associates, P.C.

(57) ABSTRACT

A method of orally administering jojoba for fat reduction, blood lipid reduction, and cancer prevention and treatment in humans is disclosed. The method incorporates a sufficient quantity of jojoba, defatted jojoba meal, jojoba extract, defatted jojoba meal extract, naturally derived or synthesized simmondsin, or any naturally derived or synthesized simmondsin derivative or analogue, including aglycon, or any mixture thereof into an individual's diet in the form of a food, dietary supplement, or drug to provide simmondsin component in an amount greater than 0.01% of one's total daily diet by weight, or 0.05 gram/day. The dosage amount and duration of the administration can vary to achieve and maintain one's desired body composition and blood lipid levels. The dosage and duration of administration are increased for cancer prevention and treatment.

23 Claims, 1 Drawing Sheet

1a: $R_1 = CN$; $R_2 = H$
1b: $R_1 = H$; $R_2 = CN$

(56) References Cited

U.S. PATENT DOCUMENTS

| | | | |
|---|---|---|---|
| 5,998,457 | A | 12/1999 | Kaddurah-Daouk |
| 6,007,823 | A | 12/1999 | Abbott et al. |
| 6,245,364 | B1 | 6/2001 | Jones et al. |
| 6,277,842 | B1 | 8/2001 | Carthron |
| 6,531,114 | B1 * | 3/2003 | Gmunder et al. ............... 424/48 |
| 6,552,171 | B2 * | 4/2003 | Howard et al. ............... 530/377 |
| 6,746,695 | B1 | 6/2004 | Martin et al. |
| 2003/0008022 | A1 | 1/2003 | Mogy |
| 2003/0023039 | A1 | 1/2003 | Howard et al. |
| 2003/0023040 | A1 | 1/2003 | Howard et al. |
| 2003/0185919 | A1 | 10/2003 | Teague et al. |
| 2004/0077839 | A1 * | 4/2004 | Howard et al. ............... 530/370 |
| 2005/0203187 | A1 * | 9/2005 | Verbiscar ..................... 514/574 |

OTHER PUBLICATIONS

Holser et al.; Industrial Crops and Products; 10 (1999); pp. 41-46.*
Rauws et al.; Arch. Toxicol.; (1982) 48:311-319.*
Univ. of AZ; Office of Arid Lands Studies; "Jojoba: A Wax-Producing Shrub of The Sonoran Desert" (1974).*
Flo, G. et al., "Effects of simmondsin on food intake, growth, and metabolic variables in lean (+/? and obese (fa/fa) Zucker rats", The British Journal of Nutrition, 1999, vol. 81, No. 2, pp. 159-167.
Booth, Albert N., et al.; Isolation of a Toxic Factor from Jojoba Meal; Life Sciences; Aug. 1974; p. 1115-1120; vol. 15; Berkley, California.
Cokelaere, M. M., et al.; Devazepide Reverses The Anorexic Effect of Simmondsin in The Rat; Journal of Endocrinology; 1995; p. 473-477; vol. 147; Great Britian.
Cokelaere, Marnix M., et al.; Evidences for a Satiating Effect of Defatted Jojoba Meal; Elsevier Science—Industrial Crops and Products—An International Publication; 1995; p. 91-96.
Cokelaere, Marnix M., et al.; Fertility in Rats after Long-Term Jojoba Meal Supplementation; American Chemical Society; 1993; p. 1449-1451; vol. 41, No. 9.
Cokelaere, Marnix M., et al.; Food Intake Inhibitory Activity of Simmondsin and Defatted Jojoba Meal: Dose-Response Curves in Rats [online] 1996 [retrieved on Sep. 27, 2001] Retrieved from Internet: <URL http:// www.hort.purdue.edu/newcrop/proceedings1996/v3-377.html>.
Cokelaere, Marnix M., et al.; Influence of Jojoba Meal Supplementation on Growth and Organ Function in Rats; American Chemical Society; 1993; p. 1444-1448; vol. 41, No. 9.
Cokelaere, Marnix M., et al.; Investigation of Possible Toxicological Influences of Simmondsin after Subacute Administration in the Rat; American Chemical Society; 1992; p. 2443-2445; vol. 40, No. 12.
Elliger, Carl A., et al.; Cyanomethylenecyclohexyl Glucoside from Simmondsin Califormica; Phytochemical Reports; Apr. 1974; p. 2319-2320; vol. 13, Berkley, California.
Elliger, Carl A., et al.; Simmondsin, an Unusual 2-Cyanomethylenecyclohexyl Glucoside from Simmondsin californica; J.C.S. Perkin I; May 1973; p. 2209-2212; Berkley, California.
Elliger, Carl A., et al.; Structure and Stereochemistry of Simmondsin; J. Org. Chem.; Apr. 1974; p. 2930-2931; vol. 39, No. 19; Berkley, California.
Medina, L.A., et al.; Elimination of Toxic Compounds, Nutritional Evaluation and Partial Characterization of Protein from Jojoba Meal; p. 423-429; Hermosillo, Sonora, Mexico, published 1988.
Medina, Luis A., et al.; Detoxified and Debittered Jojoba Meal: Biological Evaluation and Physical-Chemical Characterization; Cereal Chemistry; 1990; p. 476-479; vol. 67, No. 5.
Ngoupayou, J. D. Ngou, et al.; Jojoba Meal in Poultry Diets; Poultry Science; 1982; p. 1692-1696; vol. 61; Tucson, Arizona.
Ngoupayou, Jean Ngou, et al.; Jojoba Meal in Rabbit Diets; Nutrition Reports International; Jan. 1985; p. 11-19; vol. 31 No. 1; Tucson, Arizona.
Van Boven, M., et al.; Isolation and Structural Elucidation of Major Simmondsin Analogues in Jojoba Meal by Two-Dimensional NMR Spectroscopy; American Chemical Society; 1994; p. 2684-2687; vol. 42, No. 12.
Van Boven, M., et al.; Isolation and Structural Identification of a New Simmondsin Ferulate from Jojoba Meal; American Chemical Society; 1994; p. 1118-1121; vol. 42, No. 5.
Van Boven, M., et al.; Isolation, Purification, and Stereochemistry of Simmondsin; American Chemical Society; 1993; p. 1605-1607; vol. 41, No. 10.
Van Boven. M., et al.; Extraction and Liquid Chromatographic Method for the Determination of Simmondsin in Plasma; Elsevier Science—Journal of Chromatography B: Biomedical Applications; 1994; p. 281-285.
Van Boven. M., et al.; New Simmondsin 2'-Ferulates from Jojoba Meal; American Chemical Society; 1995; p. 1193-1197; vol. 43, No. 5.
Verbiscar, Anthony J., et al.; Detoxification of Jojoba Meal by Lactobacilli; American Chemical Society; 1981; p. 296-302; vol. 29, No. 2.

* cited by examiner

1a, R₁=CN; R₂=H
1b, R₁=H; R₂=CN

1a: R₁= CN; R₂ = H
1b: R₁= H; R₂ = CN

PREPARATION AND ADMINISTRATION OF JOJOBA PRODUCT FOR REDUCING WEIGHT, FAT AND BLOOD LIPID LEVELS AND FOR THE PREVENTION AND TREATMENT OF CANCER

CLAIM TO DOMESTIC PRIORITY

The present application is a divisional application of U.S. patent application Ser. No. 10/212,577, filed Aug. 5, 2002, now U.S. Pat. No. 7,138,134 which is a continuation-in-part of U.S. patent application Ser. No. 10/066,164, filed on Feb. 1, 2002 now abandoned. This application further claims priority to Chinese Patent Application, No. 01135290.6, filed Dec. 18, 2001.

BACKGROUND OF THE INVENTION

The present invention relates to a method for reducing fat and blood lipid levels in humans.

Obesity is defined as a body mass index of greater than 30, whereas overweight is defined as having a body mass index of greater than 25. Approximately 19% Americans are obese, and 35% are overweight. In the US, the incidence of being overweight and obese has increased dramatically in the last decade. Over $33 billion is spent each year for weight loss products ($0.5 billion alone on drugs) with 14% of adults using prescription drugs for weight loss and 7% using over the counter drugs.

Obesity is a multifactorial disease which may involve genetic, metabolic, psychosocial, and environmental factors. The great majority of obesity is probably due to a complex relationship between the many factors that regulate energy intake and utilization. Obesity is a life long disorder with adverse health consequences. Obesity is considered the second leading cause of death in the U.S. and contributes to 300,000 deaths per year. It is associated with a number of diseases, including diabetes (80% of type II diabetics are obese), hypertension, gallstones, respiratory problems, and mortality rates for certain types of cancers.

Given the large obese population and the associated problems, the area of obesity research and product development for the management of obesity has been explored, yet the problem remains. The current available weight management programs almost all take a lifetime commitment by the patients and involve painful lifestyle changes. Pharmaceutical agents designed for weight loss and fat loss, more or less, carry considerable side effects.

The major classes of these drugs are listed below with their known side effects:

Adrenergic agents: side effects include insomnia, nervousness, irritability, headache, nausea, and constipation. Some can even increase blood pressure and precipitate angina.

Serotonergic agents: withdrawn from the market after valvular heart disease was reported in patients using the combination of fenfluramine and phentermine. Sibutramine can cause headache, insomnia, constipation, and dry mouth. Increases in blood pressure and pulse rate may also occur.

Lipase inhibitors: side effects include nausea, vomiting, abdominal pain, oily spotting, fatty oily stool, flatus, fecal urgency, increased defecation, and fecal incontinence. The gastrointestinal side effects could be worse if dietary fat is not reduced.

Agents that increase energy expenditure such as ephedrine, theophylline, and thyroid hormone carry the risk of cardiac complications from hypertension, increased heart rate, and so on.

Cholecystokinin is a peptide that activates gastric vagal fibers, and triggering satiety. However, it must be administered parenterally, limiting its use dramatically.

A few disclosures describe the use of defatted jojoba meal or jojoba extract for generally for weight reduction in animals. However, there is a need for a method of making and using jojoba meal, jojoba extract, or effective compounds found in jojoba for weight loss, body fat reduction, and blood lipid level reduction in humans.

DETAILED DESCRIPTION OF VARIOUS EMBODIMENTS

This invention discloses a method of reducing body weight, body fat, and blood lipid levels in humans safely and effectively by oral administration of jojoba, defatted jojoba meal, naturally derived or synthesized simmondsin, or any naturally derived or synthesized simmondsin derivative or analogue, or mixture thereof. This precise and accurate description of the use of jojoba has numerous advantages over prior art. This invention further discloses additional methods of administration of simmondsin-containing compositions for reducing body weight, body fat, and blood lipid levels in humans. Furthermore, this invention discloses the use of simmondsin-containing compositions for the possible prevention and treatment of neoplasmic cells.

The jojoba plant, *Simmondsia chinensis*, and related species including *Simmondsia californica*, are evergreen shrubs which grow wild in Arizona, lower California, and Western Mexico. Jojoba is now cultivated commercially in Argentina, Australia, China, Egypt, Israel, Mexico, Peru, and the United States. The seeds of the jojoba plant contains 50-60% of a liquid wax, known as jojoba oil. This oil is resistant to high temperatures and pressures and has been widely used in cosmetics. The residue remained after expelling the oil is known as jojoba meal, which has a high content of proteins.

Simmondsin and simmondsin-containing jojoba meal induce food intake inhibition, emaciation and had been considered toxic before it was found that long-term administration of lower doses of simmondsin or defatted jojoba meal to growing rats induced a sustained food intake inhibition of about 20% without showing any side effects. Although there are some suggestions that the anorexia induced by defatted jojoba meal is caused by its bitter taste due to the presence of simmondsin 2'-ferulate and tannins, the facts that simmondsin itself is tasteless and that the food intake inhibition in rats can be reversed by the cholecystokinin receptor antagonist, devazepide suggested that the anorexia seen following simmondsin administration is due to stimulation of the cholecystokinin satiation system. In fact, some studies have shown that the food intake reduction induced with lower doses of defatted jojoba meal is due to satiation, and is dose related.

The present invention describes how to make and use jojoba, defatted jojoba meal, naturally derived or synthesized simmondsin, or any naturally derived or synthesized simmondsin derivative or analogue, or mixture thereof for safe and effective body weight and body fat reduction in humans. Moreover, the present invention describes how to make and use such molecules for stimulation of the human cholecystokinin hormone.

Figure 1:
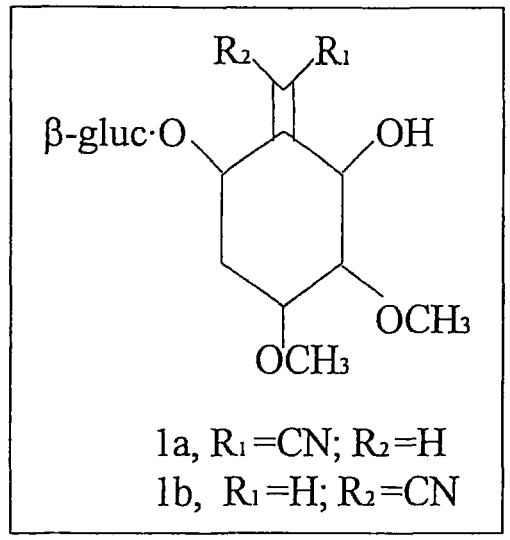
FIG. 1 is the molecular structure of the simmondsin molecule.

FIG. 1 shows the molecular structure of simmondsin. It is a multiple substituted cyclohexane system bearing a cyanomethylene substituent. The derivatives described in this invention include any molecule or compounds from the modification of simmondsin. A series of related glycosides have been extracted from the deoiled jojoba meal. The principal molecules are simmondsin [2-(cyanomethylene)-3-hydroxy-4,5-dimethoxycyclohexyl beta-D-glucoside] (up to 10% by weight of defatted jojoba meal), simmondsin 2'-ferulate, and several minor simmondsin derivatives.

We have discovered that when used properly, orally administered jojoba in humans can be safe, effective and practical. In accordance with this invention, a human is treated with a sufficient quantity of a jojoba or derived jojoba product to provide a simmondsin component of at least 0.01% of one's total daily diet by weight, or at least 0.05 gram/day, or at least 1 mg/kg body weight/day. The term "total daily diet by weight" means total weight of food consumed in a given day for a given human.

According to this invention, jojoba product includes jojoba, jojoba extract, jojoba seed, jojoba meat, fruit of jojoba, extract of jojoba seed, fruit, or meat, jojoba meal, defatted jojoba meal, jojoba meal extract, defatted jojoba meal extract, any genetically-modified organism containing or producing simmondsin or simmondsin derivatives or analogues, including the aglycon molecule, naturally derived simmondsin, synthesized simmondsin, any naturally derived or synthesized simmondsin derivative or analogue, including aglycon, or any mixture thereof.

Simmondsin component refers any molecule containing the base cyclohexane system, aglycon, that stimulates the human cholecystokinin system. Simmondsin component can be naturally derived, both in vivo in the human digestive system, and in vitro prior to consumption, from jojoba seeds, jojoba seed meal, defatted jojoba seed meal, and from other various jojoba sources or other plants. Simmondsin component can also be derived from the pure compound simmondsin (naturally derived or synthesized), from simmondsin-2'-ferulate (naturally derived or synthesized), or from related cyanomethylene glycosides (naturally derived or synthesized), or from any naturally derived or synthesized simmondsin derivatives or analogues, including aglycon, or any mixture thereof. Simmondsin component was determined by chemical analysis using gas chromatography and HPLC.

Case Studies

The following case studies and open clinical study are offered to further illustrate, but not limit the invention.

The results of the first case study are shown in Table 1 below. The subject was 26 years old and had been gradually gaining weight over the past two years. Her height was 161 cm and her weight 49 kg at the beginning of the study. Therefore her baseline BMI was 19, which was actually within the desirable range. Considering the fact that the subject was actually healthy, very low dosage of defatted jojoba seed meal was administered. The dosage form was capsules, containing 500 mg defatted jojoba seed meal per capsule.

As can be seen in Table 1, the body weight was reduced by 10% in three months with the administration of a small dosage. Hunger was noticeably reduced during the administration of the said defatted jojoba meal. No side effect was noted by the subject and blood chemistry showed no change. Body fat was greatly reduced as well via visual measurement.

TABLE 1

Use of defatted jojoba seed meal in a normal weight subject

| Time (month) | Dosage (g/day)* | Body weight (BW) | BMI |
|---|---|---|---|
| 0 | — | 49 | 19 |
| $1^{st}$ | 3 | 46 | 18 |
| $2^{nd}$ | 2 | 44 | 17 |
| $3^{rd}$ | 1 | 44 | 17 |

*Administered one hour before dinner.

The second case study was designed to determine the efficacy and safety of simmondsin administered to an obese patient in higher dosages. The subject was a 30-year-old male. At baseline, his height was 1.72 cm and weight 115 kg. His baseline BMI therefore was 39. He had an unquenchable desire to overeat since youth and every previous effort to lose weight failed.

In this case study, the simmondsin was extracted from defatted jojoba seed meal with an undisclosed method and the dosage is described as equivalent of defatted jojoba seed meal. The dosage form was an unflavored powdered shake for easy compliance. The results are shown in Table 2.

TABLE 2

Use of defatted jojoba seed meal extract in an over weight subject

| Time (month) | Dosage (g/day)* | Body weight (BW) | BMI |
|---|---|---|---|
| 0 | — | 115 | 39 |
| $1^{st}$ | 50 | 110 | 37 |
| $2^{nd}$ | 100 | 102 | 34.5 |
| $3^{rd}$ | 150 | 93.5 | 31.6 |
| $4^{th}$ | 100 | 86.6 | 29 |
| $5^{th}$ | 50 | 81.8 | 27.6 |
| $6^{th}$ | 50 | 77.6 | 26 |

*Equivalent of gram of defatted jojoba seed meal. Administered one hour before lunch and dinner in two half dosages.

The following open clinical study was designed to further evaluate the safety and efficacy of said invention in obese or over weight human subjects.

A group of 20 obese or over weight individuals with BMI higher than 25 were chosen to participate in an out patient clinical setting. The only intervention was the administration of defatted jojoba seed meal (containing 8-10% simmondsin) at 12.5 g, twice a day (one hour before lunch and dinner). The duration of the study was one month. Hunger was significantly reduced and the mean reduction of body weight was 11%. Details are summarized in Table 3. No drop-outs were reported and no side effects were observed. As can be seen in Table 3, body weight and BMI was reduced by 8.69% and 11.38%, respectively. Body fat was also dramatically decreased.

TABLE 3

Open Clinical Study With Defatted Jojoba Seed Meal

| | |
|---|---|
| Age (yr) | 29-59 |
| Baseline Body Weight | 75.5 |
| Baseline BMI | 27.5 |
| Body Weight at 1 month | 66.8 |

TABLE 3-continued

Open Clinical Study With Defatted Jojoba Seed Meal

| | |
|---|---|
| BMI at 1 month | 22.4 |
| Percent of BW reduction | 8.69% |
| Percent of BMI reduction | 11.38% |

Through the case studies small scale open clinical study discussed above, the inventors have discovered that:
1. Defatted jojoba meal is safe to use in humans.
2. Defatted jojoba meal can be used for effective reduction of body weight and body fat in humans.
3. A safe and effective dose of defatted jojoba meal, containing 10% simmondsin component, can be used in the range of 0.1-30% of one's daily diet by weight, or 0.5-600 gram/day, or 10 mg to 6 gram/kg body weight/day.
4. A safe and effective dose of extract of jojoba for the reduction of body weight and body fat can be calculated based on the findings with defatted jojoba meal described above.
5. A safe and effective dose of extract of jojoba can be used to provide simmondsin component in the range of 0.01-3% one's daily diet by weight, or 0.05-60 gram/day, or 1-600 mg/kg body weight/day (the prior art failed to define the precise dosage by specifying the length of time within with the jojoba extract is administered) in humans for the reduction of body weight and body fat.

Placebo-controlled, double-blinded clinical studies with obese and over weight human subjects are being scheduled in numerous clinical facilities in China to further demonstrate safety and efficacy. Use of a placebo-controlled and double-blinded experimental design is necessary to avoid reliance on mere anecdotal testimonies as evidence of safety and efficacy.

Aglycon—Hydrolysis of Simmondsin

Presently, defatted jojoba seed meal is readily available, with it being a by-product of oil extraction process of the seeds of the jojoba plant. It is now normally discarded. However, since it takes almost three years for jojoba crops to grow to produce the seeds, it may be necessary to find alternative source for simmondsin components. There are at least two ways to achieve this goal.

Figure 2:
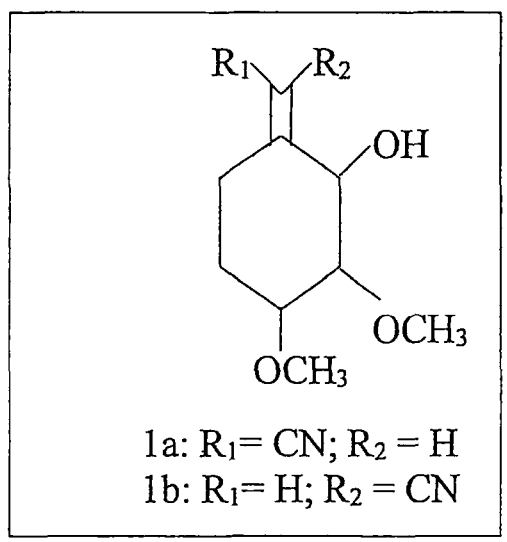
FIG. 2 is the molecular structure of the aglycon molecule.

First, our studies indicate that aglycon is the heart of the simmondsin molecule that gives simmondsin its efficacy in satiating hunger. The aglycon of simmondsin can be much more effective than simmondsin itself. The alglycon molecule is the heart of the simmondsin molecule which is responsible for simmondsin component. FIG. 2 illustrates the molecular structure of the aglycon molecule. Therefore, hydrolyzing simmondsin (as an extract or in defatted jojoba meal) down to its aglycon or other derivatives can greatly improve the efficacy of the starting materials.

The aglycon or other derivatives can be extracted into pure forms to be used as a therapeutic drug. Combining simmondsin, aglycon, or other derivatives or analogues of simmondsin with a pharmaceutically acceptable carrier will allow easy oral administration for reduction of blood lipid levels and treatment of neoplasmic cells.

Alternatively, the aglycon or other derivatives of simmondsin can be administered in any dosage forms described above with a greater efficacy in causing weight and/or fat reduction. The aglycon or other derivative of simmondsin can be just as effective when administered without being purified first. Therefore, creating a jojoba extract is not a prerequisite to hydrolyzing simmondsin to produce the aglycon molecule. The aglycon or other derivatives of simmondsin can be obtained by hydrolyzing the simmondsin in the jojoba meal, defatted jojoba meal, or an extract of jojoba. Hydrolysis can be carried out with beta-glucosidase, alkalinic agents, acids, heat or any other effective agents known in the art.

Synthesis of Aglycon and Simmondsin

Figure 3:
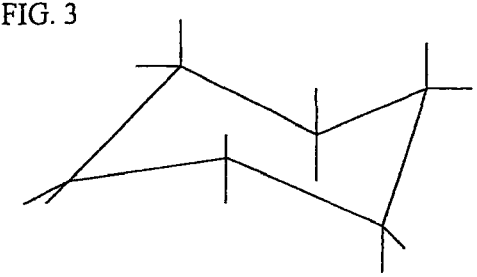
FIG. 3 is the stereochemistry of the benzene ring used in synthesizing the aglycon and simmondsin molecules.

FIG. 3 illustrates the stereochemistry of the base cyclohexane molecule of the aglycon molecule. Starting with a cyclohexane molecule with the same stereochemistry as in FIG. 3, the aglycon molecule can be synthesized by reacting the cyclohexane molecule ring in such a manner that is known in the art to cause the addition of the necessary oxygen, methane and cyano groups. The simmondsin molecule can then be synthesized by the addition of a glucose molecule. In the absence of the particular cyclohexane molecule shown in FIG. 3, a benzene ring would be a second alternative base molecule from which to synthesize aglycon and ultimately simmondsin.

Cholesterol Reducing Agent

Yet another benefit of administering simmondsin component as described according to this invention is the reduction of blood lipid levels such as triglycerides, cholesterol, and apolipoproteins due to reduced fat intake and interference with lipid synthesis in the body.

Lipids are fats or fat-like substances found in plants and animals. Cholesterol is an important lipid, which in spite of its bad press, is an essential nutrient necessary for repairing cell membranes, manufacturing vitamin D on the skin's surface, and creating hormones, such as estrogen and testosterone. The body acquires some cholesterol through diet, but about two-thirds is manufactured in the liver, its production stimulated by saturated fat. Cholesterol and some other lipids, including triglycerides, are transported in the blood packed in sphere-shaped bodies called lipoproteins. These lipoproteins are categorized into five types according to size: chylomicrons (largest in size and lowest in density), very low density lipoproteins (VLDL), intermediate density lipoproteins (IDL), low density lipoproteins (LDL), and high density lipoproteins (HDL), the smallest and most dense. Other lipid-carrier molecules coming under scrutiny are lipoprotein(a), apolipoprotein B, and so-called remnant lipoproteins, which are byproducts of chylomicrons, very low density lipoproteins (VLDL), or both.

The primary villain in the cholesterol story is low density lipoprotein (LDL). This lipid, which transports about 75% of the blood's cholesterol to the body's cells, is normally harmless. LDL does, however, penetrate the walls of the artery where it can interact dangerously through a process called oxidation, caused by unstable molecules called oxygen-free radicals. These particles are released naturally during the body's chemical processes and increase when the body is exposed to environmental toxins, such as cigarette smoke. Free radicals are essential in fighting bacteria, but in excess they can cause harm in many ways. Because they are missing an electron, free radicals tend to bind with any other molecule in the body and can thus become destructive. If LDL collects on arterial walls, free radicals released from the wall membranes attack and modify its form.

The resulting oxidized form of LDL triggers white blood cells in the immune system to gather at the site, forming a fatty substance called plaque and causing inflammation. As the plaque builds up, the arterial walls slowly constrict, reducing blood flow. This process—atherosclerosis—is the major contributor to the development of coronary heart disease; vital tissues in the heart fail to receive enough of the blood-borne oxygen they need and are damaged. In addition, the body forms calcium to wall off the inflamed area in the artery. This brittle, calcified area can be sheared off as blood flows through the artery, resulting in injury and the formation of a blood clot. If blockage occurs—caused by either the gradual build-up of plaque or by the much more rapid formation of a blood clot—the result is a heart attack. Oxidized LDL may also play another dangerous role by impairing nitric oxide, a chemical that helps relax the blood vessels, allowing blood to flow freely.

High levels of high density lipoprotein (HDL) are as important for health as low LDL levels. HDL serves to remove cholesterol from the walls of the arteries and return it to the liver. High HDL levels (above 45 mg/dl) appear to protect arteries from dangerous narrowing and so help prevent heart attacks. In one study, HDL levels below 35 mg/dl were strongly predictive of death from coronary artery disease.

Evidence now suggests that triglycerides may be major trouble-makers for the heart. Triglycerides are fat molecules packed along with cholesterol in the lipoprotein transport spheres. High triglyceride levels displace HDL cholesterol. Research also indicated that the body converts triglyceride carriers into very small dense LDL particles—more dangerous than LDL itself. Triglycerides may also be responsible for the development of blood clots that form and block the arteries, resulting in a heart attack. High triglycerides are often associated with insulin resistance, obesity (particularly around the abdomen), and diabetes.

Studies are finding an elevated risk for angina and first heart attacks in people with elevated levels of a cholesterol-carrying molecule called lipoprotein(a), or lp(a). The molecules have a structure similar to LDL and carry a protein that may deter the body's ability to dissolve blood clots and so may contribute to heart attacks. On the other hand, high levels of lp(a) may merely be by-products of long-term injury to the arteries that serve only as markers of late-stage atherosclerosis. High levels of lp(a) found in blood tests are not yet useful for accurately predicting a heart attack, although they may be helpful in prompting more aggressive treatment for people with moderate risks for heart disease. The extra danger posed by elevated levels lp(a) may be present only when cholesterol levels in general are unhealthy. High concentrations of lipoprotein(a) are usually inherited and do not respond to dietary or lifestyle changes (although they appear to increase with high intake of trans-fatty acids). At this time, few experts are recommending drug treatments to reduce lp(a) levels. Women appear to be at greater risk for high lp(a) levels than men, possibly because the male hormone testosterone prevents elevated levels, although older women are protected by hormone replacement therapy.

Apolipoprotein A-1 has been associated with healthy hearts and may be partially responsible for the lower risk for heart disease associated with high levels of HDL. However, 'Apolipoprotein B (apo B) is associated with high levels of LDL, and one study reported that it may be more effective than other lipids for predicting heart disease in women. Furthermore, remnant lipoproteins are byproducts of chylomicrons, very low density lipoproteins (VLDL), or both. Some research indicates that they may be an important risk factor for coronary artery disease.

Effects of ingestion of jojoba oil on blood cholesterol levels and lipoprotein patterns have been preliminarily demonstrated in New Zealand white rabbits. It was discovered that jojoba oil at a 2% level is highly effective in lowering blood cholesterol in rabbits on a 1% cholesterol diet over a period of 30 days.

Our own research and studies indicate that the cholesterol lowering effects reported in that study was caused by the intake of residual amounts of simmondsin and its analogues in the jojoba oil used in the experiment. Therefore, administration of jojoba product, as previously defined according to this invention, or any mixture thereof, can help reduce the production and absorption of lipids, such as cholesterol, reducing the system lipid (cholesterol) levels. More specifically, administration of simmondsin in accordance with this invention can be used to reduce LDL and/or Apolipoprotein, reduce VLDL and/or Remnant Lipoproteins, increase HDL and/or Apolipoprotein A-1, and reduce Triglycerides.

Therefore, simmondsin component-containing compositions can be used as a therapeutic agent to reduce cholesterol in humans, thereby decreasing the risk of angina and heart attacks in humans.

Chemotherapeutic Agent

The National Cancer Institute estimated that approximately 8.9 million Americans with a history of cancer were alive in 1997. Some of these individuals were considered cured, while others still had evidence of cancer and may have been undergoing treatment. About 1,284,900 new cancer cases are expected to be diagnosed in 2002. Since 1990, about 16 million new cancer cases have been diagnosed. In year 2002, about 555,500 Americans are expected to die of cancer, more than 1,500 people a day. Cancer is the second leading cause of death in the United States, exceeded only by heart disease. In the United States, 1 of every 4 deaths is from cancer. The National Institutes of Health estimate overall costs for cancer in the year 2001 at $156.7 billion: $56.4 billion for direct medical costs (total of all health expenditures); $15.6 billion for indirect morbidity costs (cost of lost productivity due to illness); and $84.7 billion for indirect mortality costs (cost of lost productivity due to premature death).

Neoplasm is defined as an abnormal growth (tumor) that starts from a single altered cell. A neoplasm may be benign or malignant. Cancer is a malignant neoplasm.

Current cancer treatments include surgery, radiation, and chemotherapy. Chemotherapy is sometimes the first choice for treating many cancers. It differs from surgery or radiation in that it is almost always used as a systemic treatment. This is important because chemotherapy can reach cancer cells that may have spread to other parts of the body. Chemotherapy drugs are divided into several categories based on how they affect specific chemical substances within cancer cells, which cellular activities or processes the drug interferes with, and which specific phases of the cell cycle the drug effects. Categories of chemotherapeutic drugs include:

Alkylating agents work directly on DNA to prevent the cancer cell from reproducing. As a class of drugs, these agents are not phase-specific (they work in all phases of the cell cycle).

Nitrosureas act in a similar way to alkylating agents. They inhibit enzymes that are needed for DNA repair.

Antimetabolites are a class of drugs that interfere with DNA and ribonucleic acid (RNA) growth.

Antitumor antibiotics have both antimicrobial and cytotoxic activity. These drugs also interfere with DNA by chemically inhibiting enzymes and mitosis or altering cellular membranes.

Mitotic inhibitors are plant alkaloids and natural products that can inhibit mitosis or inhibit enzymes that prevent protein synthesis needed for reproduction of the cell.

Other chemotherapy drugs which have slightly different mechanisms of action and do not fit into any of the above categories include such drugs as L-asparaginase, amsacrine, and tretinoin.

Many cytotoxic chemotherapy drugs work only on actively reproducing cells (not G0, the resting phase). These drugs specifically attack cells in a particular phase of the cell cycle (the M or S phases, for example). Although chemotherapy drugs attack reproducing cells, they do not distinguish between reproducing cells of normal tissues (that are replacing worn-out normal cells) and cancer cells. Therefore, chemotherapy is given to kill cancer cells, it also can damage normal cells. Normal cells that are rapidly dividing, such as blood cells, cells of hair follicles, and cells in the reproductive and digestive tracts are more likely to be damaged by chemotherapy medications. Damage to these cells account for many of the side effects of chemotherapy drugs.

Long term jojoba meal supplementation in high doses is linked to a decrease in red cell distribution width, hemoglobin concentration, mean corpuscular hemoglobin concentration, and number of white blood cells. Appetite suppression was obvious but moderate. However, no other side effects commonly associated with cancer chemotherapy were found with the administration of jojoba meal or simmondsin in animal and human studies.

Our research and studies indicate that the administration of simmondsin component when given in high doses, for example, 100-6000 mg/kg body weight per day, or in an amount greater than 0.1 g/day, over an extended time period, orally or parentally, alone or in combination with other chemotherapeutic agents or cancer treatments, may exhibit several cancer prevention and cancer treatment benefits. More specifically, administration of jojoba product as previously defined by this invention, or any combination thereof, may by used in the prevention and treatment of neoplasm by preventing cancer cells from growing and inhibiting the growth of cancer cells.

The intravenous route of chemotherapy delivery is most common. Intramuscular and subcutaneous injections are less frequently used because many drugs can be very irritating or even damaging to the skin or muscle tissue. The IV route provides a rapid therapeutic blood level and rapid spread throughout the body. IV therapy may be given by several methods.

Although oral route is preferred by most patients when it comes to self medication, some chemotherapy drugs are never taken by mouth because the digestive system cannot absorb them or because they are very irritating to the digestive system. Finding a cancer drug that has the least side effects, provides high or moderate cancer growth inhibition, and easy to take has always been the goal of cancer drug research. Since simmondsin and jojoba meal can be taken orally as a drug, dietary supplement, or in food products, jojoba meal can be used as a chemotherapeutic agent without causing gastro-intestinal tract side effects. As an additional benefit, our research reported no hair loss resulting from intake of simmondsin component or jojoba meal.

Administration of Simmondsin Component

Administration of a composition for weight loss reduction, fat reduction, cholesterol reduction, and for chemotherapeutic effect can be accomplished in numerous ways according to this invention. This invention envisions a method of administering simmondsin component in a variety of ways, alone or in combination with other therapeutic or nutritional supplements. Because simmondsin component is effective when ingested orally, numerous vehicles for delivery of simmondsin component are possible.

The method of administration with the simmondsin component can be by simply mixing it with the food the human is to consume, prepared in forms of capsules, tablets, powders, liquids, shakes, bars, candies or other confections, tea bags, or chewing gum (safe because overdose is unlikely), or any form of food. It is preferred that the simmondsin component be administered in a powder form. Powder formulae's advantage is that simmondsin component can easily be mixed with any type of food product and can be administered in a fairly large dosage.

Furthermore, administration of simmondsin component be liquid form. Simmondsin component can be administered as a drink including, but not limited to, coffee, tea, nutritional and dietary supplement drinks, milk shakes, and protein shakes.

It is also preferable that the simmondsin component can be administered sublingually in a chewing gum form. The benefits of administering the simmondsin component can be higher safety (not easy to overdose), easy to use (can be chewed any time), easy to adjust the dosage (the gums can contain a small unit dosage, such as 0.1 gram simmondsin component or 1 gram of defatted jojoba meal per gum), and more targeted use (can be chewed whenever hunger is present). The form may also be a more effective dose form because the chewing process can effectively make the simmondsin component available and enzymes from the saliva may metabolize the simmondsin component into more effective derivatives such as the aglycon of simmondsin. Less raw ingredients may be needed in this dosage form.

The method of administration with the simmondsin component can also be by integrating it into sprays or lozenges to deliver sublingually to by-pass liver metabolism. Furthermore, sublingual administration can easily be accomplished through administering simmondsin component in chewing tobacco. Similar to chewing gum, the simmondsin is released through enzymatic reactions with human saliva and has the same advantages as administration in chewing gum form.

The method of administration with the simmondsin component can also be by integrating it into injectable forms to deliver parentally to by-pass liver metabolism and for faster and stronger actions.

Alternatively, it is also preferable that the simmondsin component can be administered in a food bar form. This dosage form enables the addition of multiple nutrients to ensure adequate intake of essential nutrients, such as vitamins, minerals, amino acids, etc. to prevent potential malnutrition. Addition of flavors and sweeteners can enhance palatability. It can also be beneficial that the simmondsin component be administered in a shake form. This dosage form enables the addition of multiple nutrients to ensure adequate intake of essential nutrients, such as vitamins, minerals, amino acids, etc. to prevent potential malnutrition. Addition of flavors and sweeteners can enhance palatability. Yet another preferable way to administer the simmondsin component can be confections such as candies. This dosage form can be extremely easy to use due to the high palatability.

Since reduced food intake lead to reduced nutrient (proteins, carbohydrate, and fatty acids) intake, it can be beneficial to administer the simmondsin component with essential nutrients and nutritional supplements such as proteins, amino acids, vitamins, macro and trace minerals, or the mixture thereof. The addition of other nutritional substances such as creatine can help the body build muscle mass. Furthermore, many nutritional herbs, plant derived phytonutrients, and nutrients from any other sources can be beneficial when administered together with the above mentioned simmondsin component because they can offer added benefits such as boosting energy, minimizing fatigue, preventing acidosis, increasing metabolic rate, etc. Combining simmondsin component with proteins to make up lost protein intake due to decreased food intake, then mixing them with the food the human is to consume, prepared forms of capsules, tablets, powders, liquids, shakes, bars, candies, tea bags, or chewing gum (safe because overdose is unlikely), or any form of food.

The method of administration with the simmondsin component can also be by combining it with a supplemental dose of vitamins to make up lost vitamin intake due to decreased food intake, then mixing them with the food the human is to consume, prepared forms of capsules, tablets, powders, liquids, shakes, bars, candies, tea bags, or chewing gum (safe because overdose is unlikely), or any form of food.

The method of administration with the simmondsin component can also be by combining it with a supplemental dose of macro and trace minerals to make up lost mineral intake due to decreased food intake, then mixing them with the food the human is to consume, prepared forms of capsules, tablets, powders, liquids, shakes, bars, candies, tea bags, or chewing gum (safe because overdose is unlikely), or any form of food.

The method of administration with the simmondsin component can also be by combining it with a supplemental dose of herbal components to enhance palatability and compliance, then mixing them with the food the human is to consume, prepared forms of capsules, tablets, powders, liquids, shakes, bars, candies, tea bags, or chewing gum (safe because overdose is unlikely), or any form of food.

The method of administration with the simmondsin component can also be by combining it with a supplemental dose of creatine to help increase muscle mass, then mixing them with the food the human is to consume, prepared forms of capsules, tablets, powders, liquids, shakes, bars, candies, tea bags, or chewing gum (safe because overdose is unlikely), or any form of food.

Since reduced food intake lead to reduced nutrient (proteins, carbohydrate, and fatty acids) intake, it can be beneficial to administer the simmondsin component with essential nutrients or dietary supplements such as proteins, amino acids, vitamins, macro and trace minerals, or the mixture thereof. The addition of substances such as creatine can help the body build muscle mass.

Furthermore, many herbs, plant derived phytonutrients, and nutrients from any other sources can be beneficial when administered together with the above mentioned simmondsin component because they can offer added benefits such as boosting energy, minimizing fatigue, preventing acidosis, increasing metabolic rate, etc.

This invention also envisions combining simmondsin component with metabolite detoxification agents. Adding Calcium D-Glucarate, Potassium Glucarate, or any salt of Glucarate, or Glucaric Acid, as a metabolite detoxification agent, will help the body excrete any toxic metabolites. Detoxification of toxic metabolites assists the body in reducing fat and prevent production of new fatty tissue, as metabolite toxins are primarily stored in a human's fatty tissue.

The following molecules are also effective metabolite detoxifcation agents: N-Acetyl Cysteine (NAC), Glutathione, Indole 3 Carbinol, Diidoly-3-Methane (DIM), Conjugated Linoleic Acid (CLA), Guanine Triphosphate (GTP), Selenium, Garlic, Rosox, Milk Thistle (Silymarin), Mixed Vitamin E's, Mixed, Carotenoids, Vitamin C/Bioflavonoids, Lipoic Acid/Dihydrolipoate, Soy Isoflavones, Monoterpenes, Diterpenes, Triperpenes, and Cruciferous Vegetable Sulfer Compounds.

Finally, this invention also envisions combining simmondsin component with other weight-reducing agents to develop extra strength formulaes or create enhanced weight-reducing compositions that benefit from the unique fat-reducing properties of simmondsin component. Additionally, this invention envisions combining simmondsin component with other weight-reducing agents so that such compositions can benefit from the blood lipid level reducing properties of simmondsin component.

Method of Weight Loss and Fat Reduction

The method of achieving weight loss and fat reduction over time comprises administering varying dosages of a simmondsin component over a given period of time. The following illustrations of the weight loss and fat reduction method using simmondsin component are given as non-limiting examples only to illustrate the use of simmondsin component to produce weight loss and fat reduction in humans.

The initial dosage depends on the human's obesity level. For more obese patients, the initial dosage level should higher, for example between 100 and 200 milligrams of simmondsin component per kilogram of body weight per day. This correlates to close to about one percent simmondsin component. The dosage should then be doubled after the first month, then increased again to three times the initial dosage in third month, providing for simmondsin component of up to three percent. The dosage should be then be reduced again in the fourth month to double the initial dosage and then reduced again in the fifth month to the original dosage level. The original dosage should continue to be administered in the following months until desired weight is achieved. The step-up/step-down method of administration is illustrated in Table 2.

For less obese patients and patients not obese but desiring to lose excess body weight and reduce fat, lower dosages should be administered. Our studies indicate that in some patients, even dosages as low as one milligram of simmondsin component per kilogram of body weight per day, correlating to 0.01 percent, can satiate hunger, causing weight loss and fat reduction. However, the initial dosage should be scaled to be three times that of the final dosage and stepped down, as illustrated in Table 1 above, until desired weight is achieved.

The preferred embodiment of the invention is described above in the Drawings and Description of Various Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method of treatment of a neoplasm in a subject, comprising:

hydrolyzing or synthesizing simmondsin to produce aglycon or analog thereof;

administering an effective amount of the aglycon or analog thereof for inhibiting a growth rate of the neoplasm, wherein the effective amount of the aglycon or analog thereof is administered via a method selected from the group consisting of oral, sublingual, subcutaneous, inhalation and intravenous; and the effective amount of the aglycon or analog thereof is about 100 mg to about 6000 mg per kilogram of body weight of the subject.

2. The method of claim 1, wherein the aglycon or analog thereof is administered in a food product.

3. A method of treatment of a neoplasm in a subject, comprising:
hydrolyzing simmondsin to produce a simmondsin derivative; and
administering an effective amount of the simmondsin derivative for inhibiting growth of the neoplasm, wherein the effective amount of the simmondsin derivative is greater than 0.1 g/day.

4. The method of claim 3, wherein the effective amount is about 100 mg/kg to about 6000 mg/kg body weight of the subject.

5. The method of claim 3, wherein the simmondsin derivative is administered via a method selected from the group consisting of oral, sublingual, subcutaneous, inhalation and intravenous.

6. The method of claim 3, wherein the simmondsin derivative is administered in a food product.

7. A method of treatment of cells forming a neoplasm in a subject comprising the step of administering an effective amount of jojoba product including aglycon or analog thereof hydrolyzed or synthesized from simmondsin or analog thereof for inhibiting a growth rate of the neoplasm; and
the effective amount of the aglycon or analog thereof is greater than 0.1 g/day.

8. The method of claim 7, wherein the effective amount is about 100 mg/kg to about 6000 mg/kg body weight of the subject.

9. The method of claim 7, wherein the jojoba product is administered via a method selected from the group consisting of oral, sublingual, subcutaneous, inhalation and intravenous.

10. The method of claim 7, wherein the jojoba product is administered in a food product.

11. The method of claim 1, wherein the effective amount of the aglycon or analog thereof is administered orally.

12. The method of claim 11, wherein the aglycon or analog thereof is obtained from a residue that remains after expelling jojoba oil from jojoba seeds.

13. The method of claim 5, wherein the simmondsin derivative is administered orally.

14. The method of claim 13, further including mixing the simmondsin derivative with food that the subject is to consume.

15. The method of claim 13, further including preparing the simmondsin derivative in a form comprising a candy.

16. The method of claim 9, wherein the jojoba product is administered sublingually.

17. The method of claim 16, wherein the jojoba product is prepared in a form comprising a chewing gum.

18. A method of treatment of a neoplasm in a subject, comprising administering an effective amount of aglycon or analog thereof hydrolyzed or synthesized from simmondsin or analog thereof to reduce a growth rate of the neoplasm.

19. The method of claim 18, wherein administering the effective amount of the aglycon or analog thereof further includes administering more than 0.1 grams of the aglycon or analog thereof per day.

20. The method of claim 19, wherein administering the effective amount of the aglycon or analog thereof further includes administering about 100 to about 6000 milligrams of the aglycon or analog thereof per kilogram of the subject's body weight per day.

21. The method of claim 18, wherein administering the effective amount of the aglycon or analog thereof further includes administering the effective amount to the subject orally.

22. The method of claim 18, wherein the aglycon or analog thereof is obtained from a jojoba product that is not derived from jojoba oil.

23. The method of claim 22, wherein the aglycon or analog thereof is obtained from jojoba meal, which is a residue that remains after expelling jojoba oil from jojoba seeds.

* * * * *